US008848190B2

(12) United States Patent
Tixier et al.

(10) Patent No.: US 8,848,190 B2
(45) Date of Patent: Sep. 30, 2014

(54) SENSOR FOR EARLY DETECTION OF PROBLEMS IN ALGAE CULTURES AND RELATED SYSTEM AND METHOD

(75) Inventors: Sebastien Tixier, North Vancouver (CA); Adrian M. Fuxman, North Vancouver (CA)

(73) Assignee: Honeywell ASCa Inc., Ontario (CA)

( * ) Notice: Subject to any disclaimer, the term of this patent is extended or adjusted under 35 U.S.C. 154(b) by 218 days.

(21) Appl. No.: 13/529,240

(22) Filed: Jun. 21, 2012

(65) Prior Publication Data
US 2013/0342844 A1 Dec. 26, 2013

(51) Int. Cl.
*G01N 21/00* (2006.01)
(52) U.S. Cl.
USPC .......................................... 356/436
(58) Field of Classification Search
None
See application file for complete search history.

(56) References Cited

U.S. PATENT DOCUMENTS

| | | | | |
|---|---|---|---|---|
| 5,424,840 | A * | 6/1995 | Moore et al. | 356/410 |
| 6,028,663 | A * | 2/2000 | O'Mongain et al. | 356/213 |
| 7,324,204 | B2 * | 1/2008 | Kluczynski | 356/437 |
| 7,746,452 | B2 * | 6/2010 | Fuchigami et al. | 356/73 |
| 2009/0126265 | A1 | 5/2009 | Rasmussen et al. | |
| 2011/0136212 | A1 | 6/2011 | Parsheh et al. | |
| 2013/0030715 | A1 | 1/2013 | Tixier et al. | |

FOREIGN PATENT DOCUMENTS

| | | | |
|---|---|---|---|
| CN | 101303337 A | * | 11/2008 |
| CN | 201765187 U | | 3/2011 |
| CN | 102103084 B | | 12/2012 |
| WO | WO 2011/097261 A1 | | 8/2011 |
| WO | WO 2012/092666 A1 | | 7/2012 |

OTHER PUBLICATIONS

Notification of Transmittal of the International Search Report and the Written Opinion of the International Searching Authority, or the Declaration dated Aug. 27, 2012 in connection with International Patent Application No. PCT/CA2012/000467.
"The AlgaeTorch", bbe moldaenke, www.bbe-moldaenke.de, Nov. 2008, 1 page.
"The NEW bbe AlgaeTorch", bbe moldaenke, www.bbe-moldaenke.de, Nov. 2008, 1 page.
"Turbidity Measurement at no extra cost!", bbe moldaenke, www.bbe-moldaenke.de, Aug. 2010, 2 pages.
Susan Award, et al., "Effect of Cadmium on the growth of Chiamydomonas", The Journal of Yong Investigators: An Undergraduate, Peer-Reviewed Science Journal, vol. 13, Issue 3, Aug. 31, 2005, 9 pages.
M. Beutler, et al., "A fluorometric method for the differentiation of algal populations in vivo and in situ", Photosynthesis Research, vol. 72, 2002, p. 39-53.

(Continued)

*Primary Examiner* — Tarifur Chowdhury
*Assistant Examiner* — Amanda Merlino

(57) ABSTRACT

A method includes measuring intensities of light passing through a sample of an algae culture at different wavelengths. The method also includes identifying, using the measured intensities, a peak absorption wavelength of at least one type of chlorophyll in the sample and/or an absorption ratio involving multiple types of chlorophyll in the sample. The method further includes determining whether the algae culture has a problem using the peak absorption wavelength and/or the absorption ratio. The peak absorption wavelength could be identified by identifying a specified wavelength at which a smallest amount of light passes through the sample. The absorption ratio could be identified by identifying an average absorption wavelength of first and second types of chlorophyll in the sample and identifying a peak absorption wavelength of the first type of chlorophyll.

20 Claims, 6 Drawing Sheets

(56) References Cited

OTHER PUBLICATIONS

"FluoroProbe, Submersible Spectrofluorometer with Automatic Algae Class and Chlorophyll Analysis", bbe moldaenke, www.bbe-moldaenke.de, 4 pages.

"The new FluoroProbe III", bbe moldaenke, ww.bbe-moldaenke.de, 2008, 1 page.

"Fluorometer and Scattering Meter", WET labs ECO FLNTU; WET Labs, Inc., www.wetlabs.com Sep. 21, 2010, 1 page.

Notification of Transmittal of the International Search Report and the Written Opinion of the International Searching Authority, or the Declaration dated Apr. 10, 2012 in connection with International Patent Application No. PCT/CA2012/000005.

International Search Report dated Sep. 6, 2013 in connection with International Patent Application No. PCT/CA2013/000510, 3 pages.

Written Opinion of International Searching Authority dated Sep. 6, 2013 in connection with International Patent Application No. PCT/CA2013/000510, 7 pages.

* cited by examiner

SENSOR FOR EARLY DETECTION OF PROBLEMS IN ALGAE CULTURES AND RELATED SYSTEM AND METHOD

TECHNICAL FIELD

This disclosure relates generally to sensors for algae cultures. More specifically, this disclosure relates to a sensor for early detection of problems in algae cultures and related system and method.

BACKGROUND

Algae generally includes a large and diverse group of simple, typically autotrophic organisms that grow using photosynthesis. Photosynthesis is a process where plants generate higher-order organic compounds, such as sugars, using chlorophyll. Chlorophyll is generally characterized by a green pigment found in most living plants, and multiple types of chlorophyll can be present in an algae culture.

Algae cultures, such as those in open ponds, can become contaminated or change in a number of ways. Maintaining algae monocultures in large-scale systems is challenging as bacteria, fungus, and viruses can grow alongside the algae and compete for nutrients or otherwise disrupt the culture. A population of predators (such as zooplankton) can also grow, feeding directly from algae cells. Finally, environmental conditions such as the amount of sunlight, water temperature, and nutrient availability can change over time. All of these can lead to stressing of the algae culture, which can lead to changes in the dominant algae species, a decrease in the productivity of the algae culture, or even a complete loss of the algae culture.

SUMMARY

This disclosure provides a sensor for early detection of problems in algae cultures and related system and method.

In a first embodiment, a method includes measuring intensities of light passing through a sample of an algae culture at different wavelengths. The method also includes identifying, using the measured intensities, a peak absorption wavelength of at least one type of chlorophyll in the sample and/or an absorption ratio involving multiple types of chlorophyll in the sample. The method further includes determining whether the algae culture has a problem using the peak absorption wavelength and/or the absorption ratio.

In a second embodiment, an apparatus includes at least one interface configured to receive measured intensities of light passing through a sample of an algae culture at different wavelengths. The apparatus also includes at least one processing device configured to identify, using the measured intensities, a peak absorption wavelength of at least one type of chlorophyll in the sample and/or an absorption ratio involving multiple types of chlorophyll in the sample. The at least one processing device is also configured to determine whether the algae culture has a problem using the peak absorption wavelength and/or the absorption ratio.

In a third embodiment, a non-transitory computer readable medium embodies a computer program. The computer program includes computer readable program code for receiving measured intensities of light passing through a sample of an algae culture at different wavelengths. The computer program also includes computer readable program code for identifying, using the measured intensities, a peak absorption wavelength of at least one type of chlorophyll in the sample and/or an absorption ratio involving multiple types of chlorophyll in the sample. The computer program further includes computer readable program code for determining whether the algae culture has a problem using the peak absorption wavelength and/or the absorption ratio.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 8, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

Figure 1:
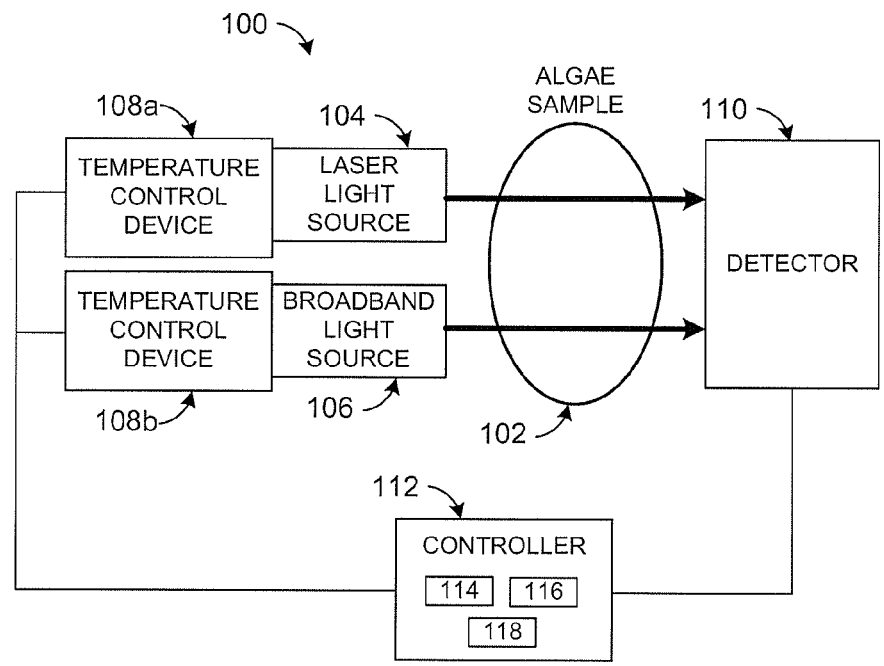
FIG. 1 illustrates an example sensor for early detection of problems in an algae culture according to this disclosure.

FIG. 1 illustrates an example sensor 100 for early detection of problems in an algae culture according to this disclosure. In this example, the sensor 100 is used to analyze an algae sample 102. The algae sample 102 represents a sample of algae taken from a larger algae culture. The larger algae culture could represent any suitable algae culture, such as an algae culture in an open or closed system. As noted above, various factors (such as bacteria, fungus, viruses, predators, or environmental conditions) can stress the algae culture. The sensor 100 uses measurements associated with one or more types of chlorophyll in the algae sample 102 to detect stress or other problems early. Ideally, corrective action can then be initiated to reduce or eliminate the problem. This can enable more effective continuous, near-continuous, or intermittent health monitoring of algae cultures, which is often important to the commercial viability of the algae industry.

As shown in FIG. 1, the sensor 100 includes multiple light sources 104-106, which generate light used to illuminate the algae sample 102. The light source 104 generates light at a controllable wavelength or within a very narrow range of wavelengths. The light source 106 is more of a broadband light source that generates light within a larger range of wavelengths.

Each light source 104-106 includes any suitable structure for generating light at the desired wavelength(s). In some embodiments, the light source 104 represents at least one diode laser, while the light source 106 represents at least one light emitting diode (LED). In particular embodiments, the light source 104 generates light at a wavelength around 675 nm, and the wavelength can change based on the temperature of the light source 104. Also, in particular embodiments, the light source 106 generates light within a band about 100 nm wide centered around 675 nm, and the average wavelength changes based on the temperature of the light source 106. Note that any other suitable light source(s) could be used to generate the desired light for the sensor 100.

The sensor 100 also includes temperature control devices 108a-108b. The temperature control devices 108a-108b can alter the temperatures of the light sources 104-106 to vary the wavelengths of light emitted by the light sources. Each temperature control device 108a-108b includes any suitable structure for altering or controlling the temperature of at least one light source. Each temperature control device 108a-108b could, for example, represent a Peltier cooler. Note that a temperature control device 108a-108b could physically contact one or more light sources, or the temperature control device 108a-108b could be located near or otherwise affect the temperature of one or more light sources without actually contacting the light source(s).

At least one detector 110 measures light from the light sources 104-106 that passes through the algae sample 102. For example, each detector 110 could measure the intensity of light passing through the algae sample 102. Each detector 110 includes any suitable structure for measuring the light that passes through an algae sample. In particular embodiments, each detector 110 could represent a silicon photodetector or other detection device. Note that a single detector 110 could be used to measure the light passing through the algae sample 102 from both light sources 104-106, or multiple detectors 110 could be used to measure the light passing through the algae sample 102 from different light sources 104-106.

A controller 112 receives measurements from the detector(s) 110. The controller 112 can use the measurements to determine how to adjust operation of the temperature control devices 108a-108b. For example, as described in more detail below, the light source 104 can be used to identify the peak absorption wavelength of at least one type of chlorophyll (such as "chlorophyll a") in the algae sample 102. Also, as described in more detail below, the light source 106 can be used to identify at least one absorption ratio involving different types of chlorophyll in the algae sample 102, such as the ratio of "chlorophyll a" absorption to "chlorophyll b" absorption. To support these functions, the controller 112 can use the temperatures of the light sources 104-106 to identify the wavelengths of light currently emitted from the light sources 104-106. The controller 112 can then adjust the temperatures of the light sources 104-106 using the temperature control devices 108a-108b to obtain a desired wavelength or wavelength range of illumination. The relationship between the temperature of a light source and the wavelength emitted by the light source is typically substantially constant over the lifetime of the light source and can be obtained in any suitable manner, such as in the factory.

The controller 112 can also analyze the measurements from the detector(s) 110 to determine if the measurements indicate stress or other problems with the larger culture. As described in more detail below, this can involve the controller 112 detecting a change in the peak absorption wavelength of one type of chlorophyll and/or a change in the absorption ratio involving different types of chlorophyll in the algae sample 102. A change beyond a threshold amount can indicate that the algae culture is experiencing stress or other problems. If a problem is detected, the controller 112 could take any suitable corrective action.

The controller 112 includes any suitable structure(s) for controlling the generation of light used to test an algae culture and/or to detect problems in the algae culture. The controller 112 could, for example, include at least one processing device 114, such as at least one microprocessor, microcontroller, digital signal processor (DSP), field programmable gate array (FPGA), application specific integrated circuit (ASIC), or other processing device. The controller 112 could also include at least one memory device 116, which could store instructions and data used, generated, or collected by the processing device(s) 114. The memory device(s) 116 could include any suitable volatile and/or non-volatile storage and retrieval device(s). In addition, the controller 112 could include at least one interface 118 for transmitting data (such as light measurements or indications of identified stress) to an external device or system or for receiving data (such as configuration data). The interface(s) 118 could represent any suitable wired or wireless interface(s), such as a wired Ethernet interface or a wireless radio frequency (RF) transceiver. Note that the controller 112 could be implemented within a single device or system, or the controller 112 could be implemented using multiple local or distributed devices.

In the above description, the controller 112 has been described as using changes in both the peak absorption wavelength of one type of chlorophyll and the absorption ratio involving different types of chlorophyll in the algae sample 102 to identify stress. It should be noted that either one or both of these characteristics could be used to identify problems in an algae culture. In other words, the controller 112 could determine whether only the peak absorption wavelength of one type of chlorophyll experiences a threshold change, only the absorption ratio involving different types of chlorophyll experiences a threshold change, or both experience a threshold change. If only the peak absorption wavelength is used, the light source 106 and its temperature control device 108b could be omitted from the sensor 100.

The sensor 100 shown here could be used in various settings. For example, in some embodiments, the sensor 100 could be used within a laboratory setting to test algae samples 102 from various ponds, tanks, or other locations. In other embodiments, various components of the sensor 100 could be placed within a housing and used in situ or on-site at a pond, tank, or other location. The sensor 100 could be portable or fixed, and any suitable mechanism could be used to manually or automatically draw an algae sample 102 into the sensor 100 for measurement.

Although FIG. 1 illustrates one example of a sensor 100 for early detection of problems in an algae culture, various changes may be made to FIG. 1. For example, various components in FIG. 1 could be combined, further subdivided, or omitted and additional components could be added according to particular needs.

As specific examples, one of the light sources 104-106 could be omitted as described above, or multiple detectors 110 could be used. As another specific example, the functionality of the controller 112 could be divided between one or multiple components. Also, the controller 112 could be implemented as a distributed system with one or more components within the sensor 100 and one or more components outside the sensor 100. As an example, a controller component within the sensor 100 could receive measurements from the detector(s) 110 and adjust the temperature control devices 108a-108b. A controlled component within an external control system could separately receive the measurements from the detector(s) 110 and determine whether the algae culture is under stress or having some other problem.

Figure 2:
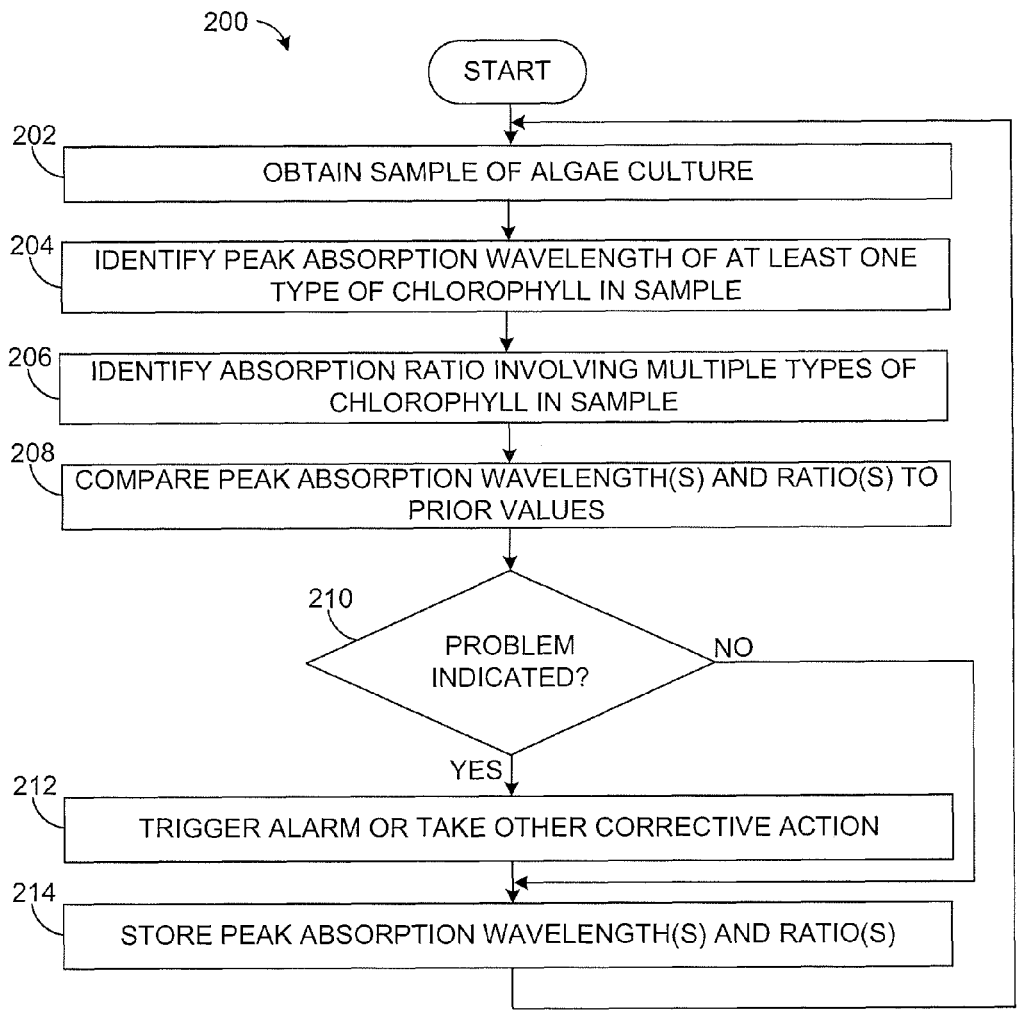
FIGS. 2 through 4 illustrate an example method for early detection of problems in an algae culture and related details according to this disclosure.
Figure 3:
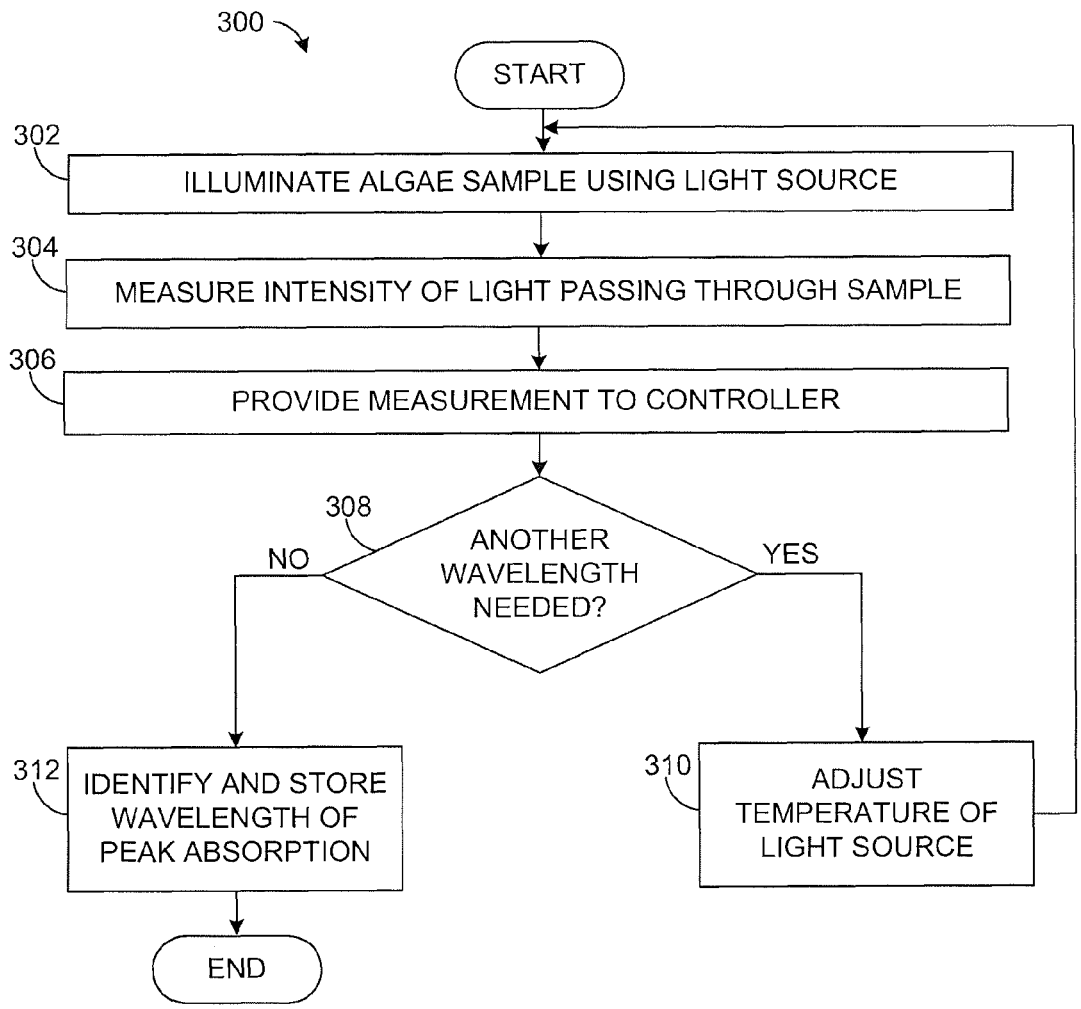
Figure 4:
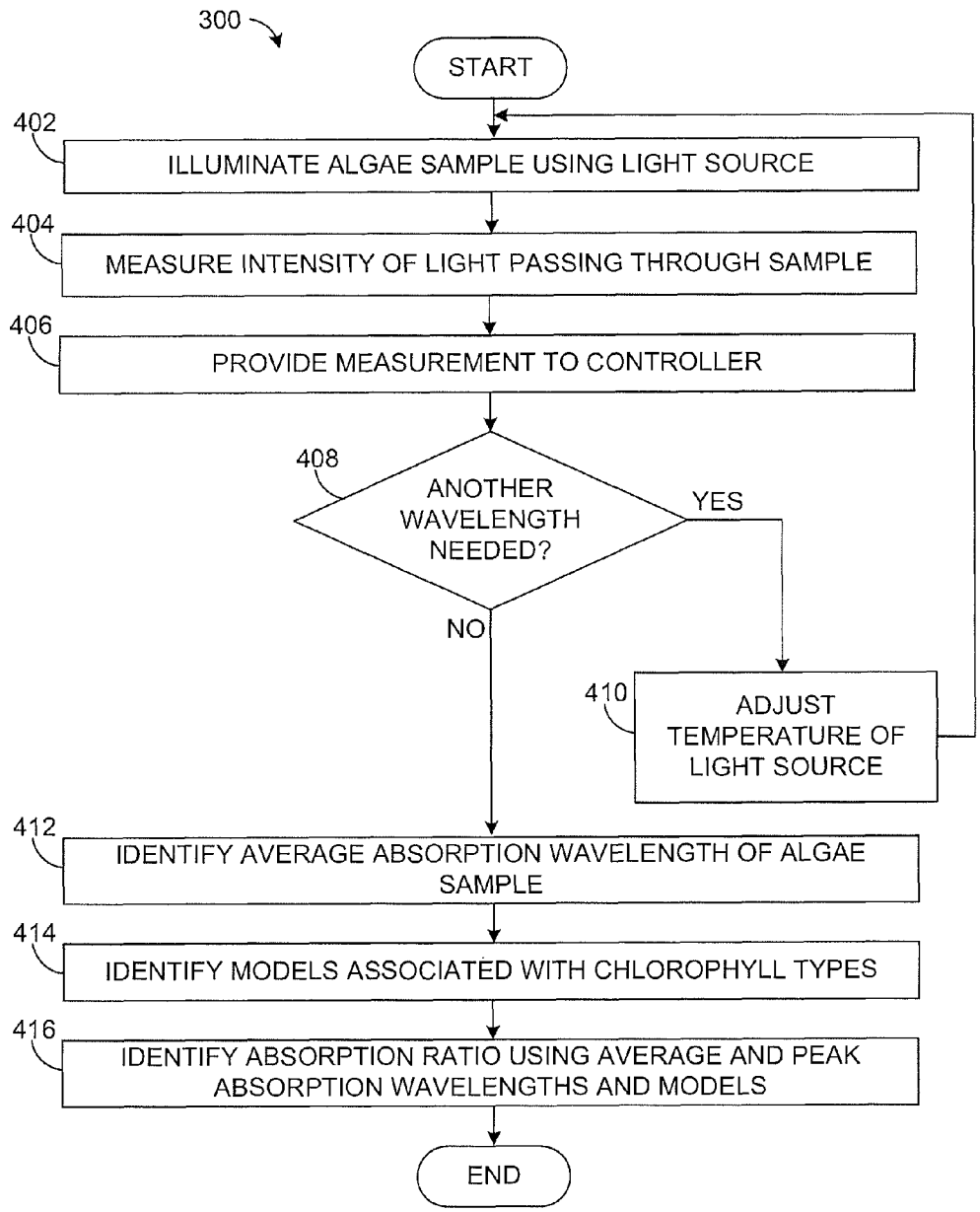

FIGS. 2 through 4 illustrate an example method for early detection of problems in an algae culture and related details according to this disclosure. In particular, FIG. 2 illustrates an example method 200 for early detection of problems in an algae culture, while FIGS. 3 and 4 illustrate example ways of implementing various steps in FIG. 2.

As shown in FIG. 2, a sample of an algae culture is obtained at step 202. This could include, for example, obtaining an algae sample 102 and placing the algae sample 102 within the sensor 100. This could occur manually or in an automated manner. This could also occur at any suitable interval.

At least one peak absorption wavelength of at least one type of chlorophyll in the algae sample is identified at step 204. This could include, for example, the sensor 100 using the light source 104 to illuminate the algae sample 102. This could also include the sensor 100 using the temperature control device 108a to control the temperature of the light source 104 to alter the wavelength(s) of light emitted by the light source 104. The amount of wavelength variation could be relatively small, such as 5 nm or 10 nm around the expected peak absorption wavelength. This could further include the controller 112 identifying the wavelength at which the least amount of light passes through the algae sample 102. This wavelength can be identified using the temperature of the light source 104 at which the least amount of light passes through the algae sample 102.

At least one absorption ratio involving multiple types of chlorophyll in the algae sample is identified at step 206. This could include, for example, the sensor 100 using the light source 106 to illuminate the algae sample 102. This could also include the sensor 100 using the temperature control device 108b to control the temperature of the light source 106 to alter the wavelength(s) of light emitted by the light source 106. The light emitted by the light source 106 could cover a relatively large range of wavelengths, such as a 100 nm-wide band. This could further include the controller 112 identifying the average absorption wavelength of multiple types of chlorophyll in the algae sample 102 and using that, together with the peak absorption wavelength, to identify the absorption ratio involving the multiple types of chlorophyll in the algae sample 102.

The at least one peak absorption wavelength and the at least one absorption ratio are compared to prior values at step 208, and a determination is made whether the comparison indicates stress or other problems in the algae culture at step 210. This could include, for example, the controller 112 comparing the current peak absorption wavelength of chlorophyll a in the current algae sample 102 to the peak absorption wavelength(s) of chlorophyll a in one or more previous algae samples 102. If the current peak absorption wavelength differs from a previous peak absorption wavelength, such as by a threshold amount, this could be indicative of a problem. Similarly, this could include the controller 112 comparing the current absorption ratio involving chlorophyll a and chlorophyll b in the current algae sample 102 with the ratio(s) of one or more previous algae samples 102. If the current ratio differs from a previous ratio, such as by a threshold amount, this could also be indicative of a problem.

If a problem is identified, an alarm is triggered or other corrective action is taken at step 212. This could include, for example, the controller 112 triggering an audio, visual, or other alarm on a control panel used by an operator. This could also include the controller 112 initiating transmission of a warning message to an operator's display or mobile device. This could further include the controller 112 automatically implementing various adjustments to the algae culture to try and reduce the problem with the culture.

The peak absorption wavelength(s) and absorption ratio(s) are stored at step 214. This could include, for example, the controller 112 storing these values in the memory device 116. The method 200 returns to step 202 to obtain another sample of the algae culture, and the stored values can be compared to new values to detect problems.

FIG. 3 illustrates an example method 300 for identifying a peak absorption wavelength of one type of chlorophyll in an algae sample, which could be performed during step 204 in the method 200. As shown in FIG. 3, an algae sample is illuminated using a light source at step 302. This could include, for example, the sensor 100 illuminating the algae sample 102 using the light source 104. The intensity of the light passing through the algae culture is measured at step 304. This could include, for example, the detector 110 measuring the light from the light source 104 that is passing through the algae culture 102. The resulting measurement is provided to a controller at step 306. This could include, for example, the detector 110 providing the intensity measurement to the controller 112 for storage in the memory device 116.

A determination is made whether another wavelength of light is needed at step 308. This could include, for example, the controller 112 determining whether the algae sample 102 has been illuminated using all wavelengths within a narrow wavelength range. If not, the temperature of the light source is adjusted at step 310, and the method returns to step 302. This could include, for example, the controller 112 causing the temperature control device 108a to alter the temperature of the light source 104 to thereby change the wavelength of light emitted from the light source 104.

If no additional wavelengths are needed, the wavelength of peak absorption in the algae sample is identified at step 312. This could include, for example, the controller 112 identifying the wavelength at which the smallest intensity of light is measured. As a particular example, this could include the controller 112 identifying the temperature of the light source 104 associated with the highest absorption and then identifying the wavelength based on the temperature. This wavelength represents the peak absorption wavelength of the specified type of chlorophyll in the algae sample.

In this way, the controller 112 can ensure that the algae sample 102 is illuminated using different wavelengths within a specified range, such as a 5 nm or 10 nm range. Note that any suitable interval between wavelengths within the range could be used, such as 1 nm or 0.5 nm intervals within the wavelength range. Also note that not all wavelengths in the range may be used during the method 300. For instance, the controller 112 may recognize that the peak absorption wavelength has already been passed during a scan of the algae sample 102, such as by looking at the measured intensity trend and determining that a change in sign in the derivative of the intensity with wavelength indicates that the peak absorption wavelength has just been passed.

Figure 5:
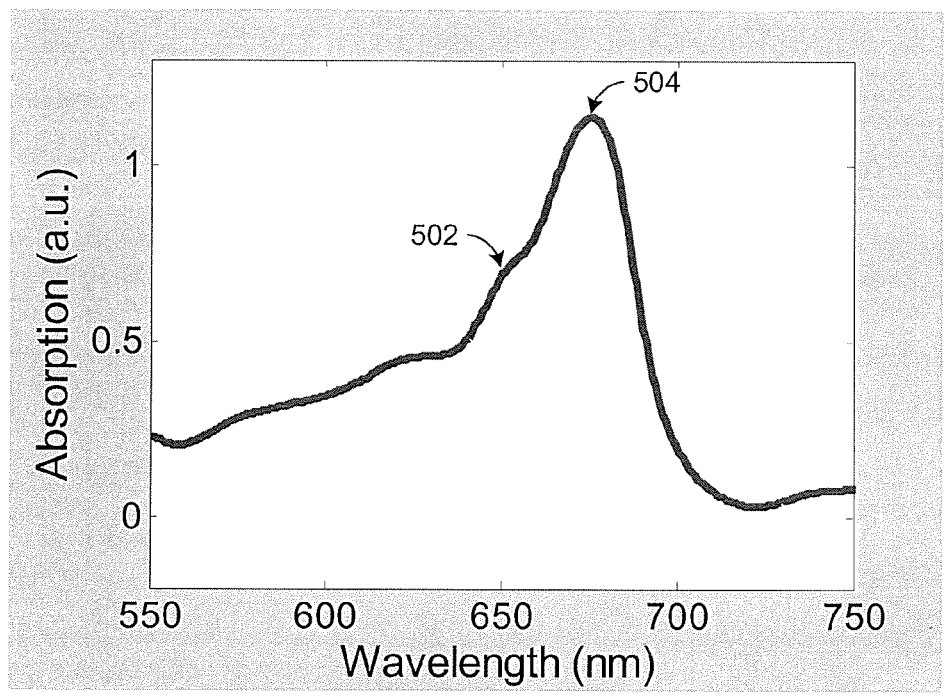
FIGS. 5 and 6 illustrate an example absorption spectrum and an example peak absorption wavelength associated with a single type of chlorophyll in an algae culture according to this disclosure.
Figure 6:
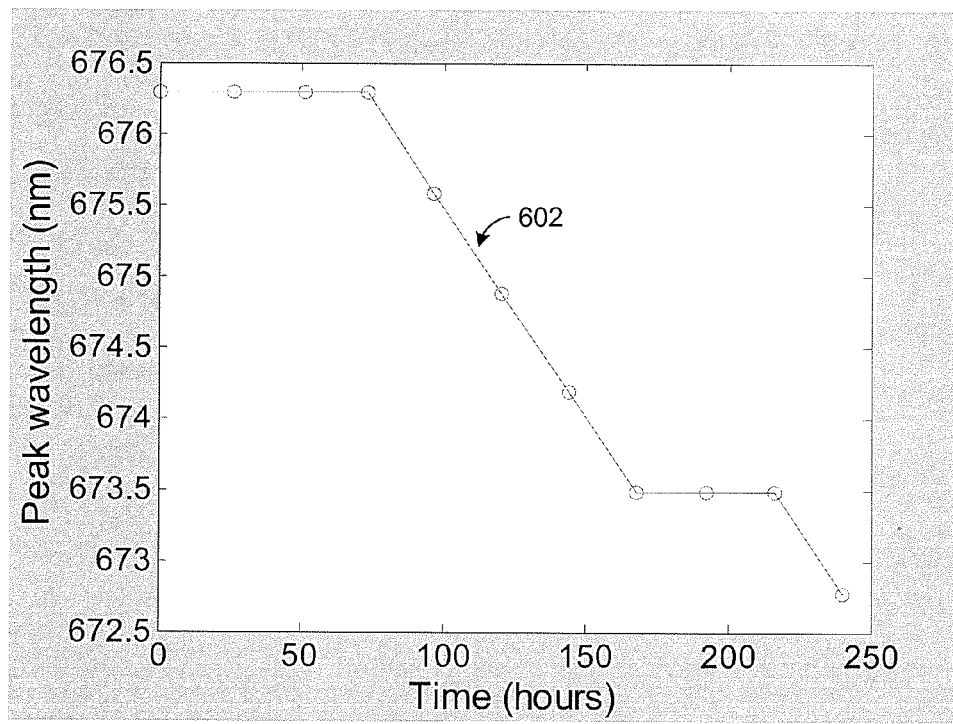

An example use of the peak absorption wavelength is shown in FIGS. 5 and 6, which illustrate an example absorption spectrum and an example peak absorption wavelength associated with a single type of chlorophyll in an algae culture according to this disclosure. In particular, FIGS. 5 and 6 illustrate an example absorption spectrum and an example peak absorption wavelength associated with chlorophyll a.

In FIG. 5, a line 502 represents an example absorption spectrum associated with chlorophyll a. As shown here, the absorption spectrum has a peak 504 around 675 nm. The peak absorption wavelength represents the wavelength where the most amount of light is absorbed by chlorophyll a. However, the peak absorption wavelength is not fixed, and the peak absorption wavelength of chlorophyll a (or other types of chlorophyll) can change slightly when an algae culture is under stress.

FIG. 6 illustrates example changes to the peak absorption wavelength associated with a single type of chlorophyll. In particular, a line 602 illustrates changes to the peak absorption wavelength of chlorophyll a as an algae culture is exposed to a high flow of carbon dioxide ($CO_2$) gas for a number of hours. The high gas flow creates a dramatic change in environmental conditions that can cause stress in the algae culture.

As shown in FIG. 6, the peak absorption wavelength of chlorophyll a in the algae culture is initially around 676.25 nm and remains substantially unchanged for about 60 hours. For about 100 hours after that, the peak absorption wavelength of chlorophyll a in the algae culture steadily declines from about 676.25 nm to about 673.5 nm. After about 50 hours more, the peak absorption wavelength of chlorophyll a in the algae culture declines again to about 672.75 nm.

Note that these values relate to a specific algae culture exposed to a specific gas flow, and other algae cultures could react differently to the same gas flow or a different gas flow. Still, FIG. 6 illustrates that changes in the peak absorption wavelength of at least one type of chlorophyll in an algae sample (in this case chlorophyll a) can be indicative of stress or other problems in an algae culture.

With this in mind, the sensor 100 can use the light source 104 to generate light at specific wavelengths, such as within a narrow range around the expected peak absorption wavelength of a particular type of chlorophyll. The sensor 100 uses measurements from the detector 110 to identify the wavelength at which the smallest amount of light passes through the algae sample 102, which is also the wavelength at which the peak amount of light is absorbed by the algae sample 102. By performing this test on multiple samples 102 of an algae culture over time, the sensor 100 can detect changes in the peak absorption wavelength of the algae culture. The controller 112 could determine if a problem is detected using these measurements, such as by determining whether the peak absorption wavelength experiences a threshold amount of change within a specified time period.

Note that the use of the peak absorption wavelength of chlorophyll a is for illustration only. The peak absorption wavelength(s) of other type(s) of chlorophyll could also be used to detect stress or other problems in an algae culture. For instance, the peak absorption wavelength of chlorophyll b is typically around 650 nm. A similar procedure as that described above could be used to detect changes in the peak absorption wavelength within a small range of wavelengths around 650 nm.

FIG. 4 illustrates an example method 400 for identifying an absorption ratio involving different types of chlorophyll in an algae sample, which could be performed during step 206 in the method 200. As shown in FIG. 4, an algae sample is illuminated using a light source at step 402. This could include, for example, the sensor 100 illuminating the algae sample 102 using the light source 106. The intensity of the light passing through the algae culture is measured at step 404. This could include, for example, the detector 110 measuring the intensity of the light that is passing through the algae culture 102. The resulting measurement is provided to a controller at step 406. This could include, for example, the detector 110 providing the intensity measurement to the controller 112 for storage in the memory device 116.

A determination is made whether another wavelength of light is needed at step 408. This could include, for example, the controller 112 determining whether the algae sample 102 has been illuminated using various wavelengths within a broader wavelength range. If not, the temperature of the light source is adjusted at step 410, and the method returns to step 402. This could include, for example, the controller 112 causing the temperature control device 108b to alter the temperature of the light source 106 to thereby change the wavelength of light emitted from the light source 106.

If no additional wavelengths are needed, the average absorption wavelength of the algae sample is identified at step 412. This could include, for example, the controller 112 calculating the average of (i) a peak absorption wavelength of chlorophyll a and (ii) a peak absorption wavelength of chlorophyll b. Absorption models associated with different chlorophyll types are identified at step 414. This could include, for example, the controller 112 identifying Gaussian or other absorption models for chlorophyll a and chlorophyll b. The absorption ratio involving two chlorophyll types is identified using the average absorption wavelength of the algae sample, the absorption models, and the peak absorption wavelength at step 416. This could include, for example, the controller 112 identifying the peak absorption wavelength calculated as shown in FIG. 3. With the peak absorption wavelength of one chlorophyll type, the average absorption wavelength of multiple chlorophyll types, and the absorption models, the controller 112 can identify the absorption ratio involving the multiple chlorophyll types.

Figure 7:
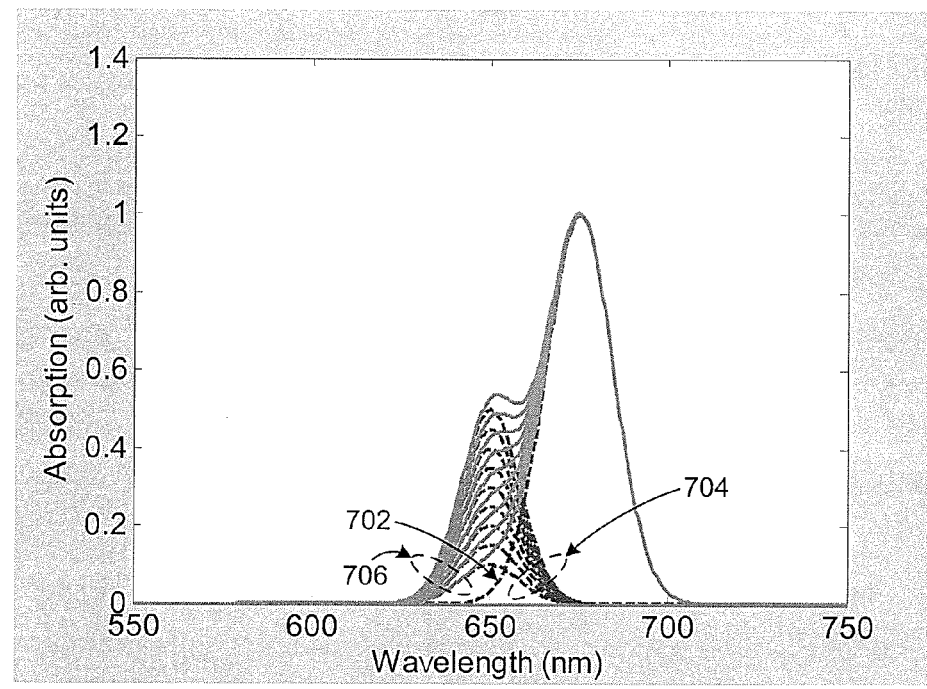
FIGS. 7 and 8 illustrate example absorption spectra and absorption ratios associated with multiple types of chlorophyll in an algae culture according to this disclosure.
Figure 8:
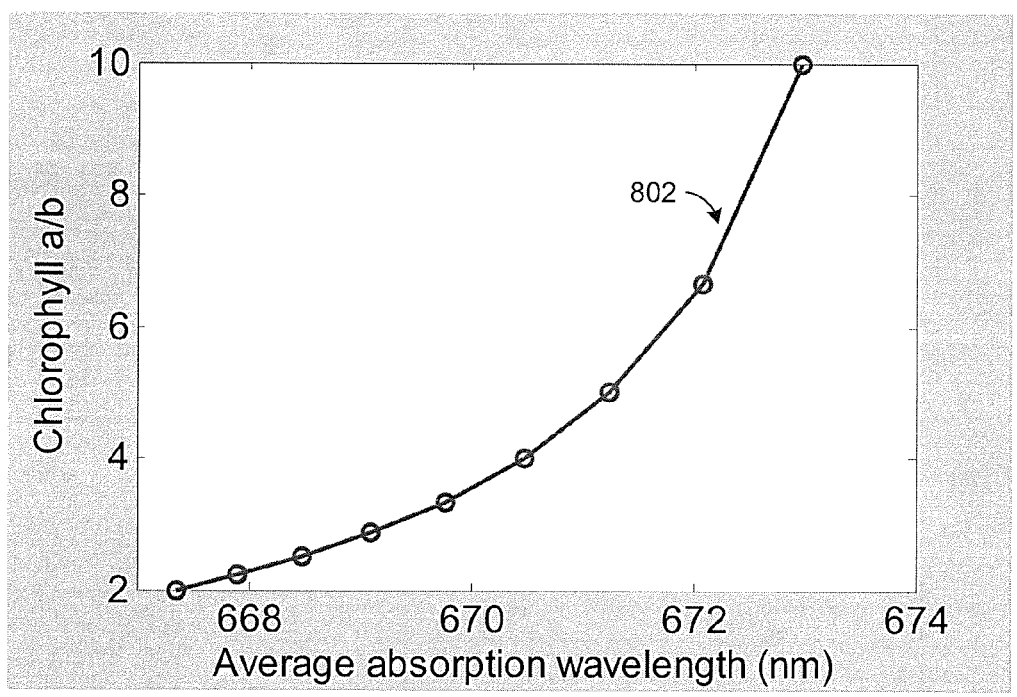

An example use of the absorption ratio involving multiple chlorophyll types is shown in FIGS. 7 and 8, which illustrate example absorption spectra and absorption ratios associated with multiple types of chlorophyll in an algae culture according to this disclosure. In particular, FIG. 7 illustrates example absorption spectra associated with different combinations of chlorophyll a and chlorophyll b, and FIG. 8 illustrates example average absorption wavelengths associated with different combinations of chlorophyll a and chlorophyll b.

In FIG. 7, a dashed line 702 denotes the absorption spectrum associated with a specified amount of chlorophyll a. Also, dashed lines 704 denote the absorption spectra associated with different amounts of chlorophyll b. In addition, solid lines 706 represent different sums of the absorption spectrum for chlorophyll a and the different absorption spectra for chlorophyll b.

As can be seen here, larger quantities of chlorophyll b result in larger absorption measurements around 650 nm, while smaller quantities of chlorophyll b result in smaller absorption measurements around 650 nm. Combining the absorption measurement around 650 nm (for chlorophyll b) with the absorption measurement around 675 nm (for chlorophyll a) therefore results in an average measurement that varies based on the absorption ratio of chlorophyll a and chlorophyll b. With knowledge of the peak absorption wavelength of one type of chlorophyll (chlorophyll a in this example) and the average absorption wavelength, the absorption models can be used to identify the amount of another type of chlorophyll (chlorophyll b in this example). This allows the absorption ratio involving multiple chlorophyll types to be determined.

FIG. 8 illustrates an example relationship between the average absorption wavelength and the chlorophyll a/chlorophyll b absorption ratio. This relationship can be determined using different combinations of a specified amount of chlorophyll a and different amounts of chlorophyll b. In FIG. 8, a line 802 identifies how the chlorophyll a/chlorophyll b absorption ratio varies based on the average absorption wavelength. Again, note that these values relate to a specific algae culture, and other algae cultures could have different values.

With this in mind, the sensor 100 can use the light source 106 to generate light within a wavelength range, such as within a range that includes the peak absorption wavelengths of multiple types of chlorophyll. The sensor 100 uses measurements from the detector 110 to identify the average absorption wavelength of the algae sample 102. Using the peak absorption wavelength identified using the light source 104, the average absorption wavelength, and the absorption models, the controller 112 can identify the absorption ratio involving different types of chlorophyll in the algae sample 102. By performing this test on multiple samples 102 of an algae culture over time, the sensor 100 can detect changes in the absorption ratio over time. The controller 112 could determine if a problem is detected using these measurements, such as by determining whether the absorption ratio experiences a threshold amount of change within a specified time period.

Note that the use of the ratio of chlorophyll a absorption to chlorophyll b absorption is for illustration only. Other ratios of chlorophyll absorptions could also be used to detect problems in an algae culture. For instance, the ratio of chlorophyll b absorption to chlorophyll a absorption could be used, or a ratio involving the absorptions by other type(s) of chlorophyll could be used.

Although FIGS. 2 through 4 illustrate one example of a method 200 for early detection of problems in an algae culture and related details, various changes may be made to FIGS. 2 through 4. For example, while shown as a series of steps, various steps in each figure could overlap, occur in parallel, occur in a different order, or occur any number of times. Also, as noted above, only peak absorption wavelength changes or only absorption ratio changes could be used to identify problems in an algae culture.

In addition, note that the various graphs shown in FIGS. 5 through 8 are for illustration only. Various graphs shown here are simulated or relate to a specific algae sample. These graphs are meant to help illustrate various details of the methods in FIGS. 2 through 4 and do not limit this disclosure to any particular absorption spectra, peak absorption wavelengths, or absorption ratios.

In some embodiments, various functions described above are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The terms "transmit" and "receive," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. A method comprising:
   measuring intensities of light passing through a sample of an algae culture at different wavelengths;
   identifying, using the measured intensities, an average absorption wavelength of first and second types of chlorophyll in the sample and a peak absorption wavelength of the first type of chlorophyll;
   identifying an absorption ratio involving the first and second types of chlorophyll using the average absorption wavelength, the peak absorption wavelength, and at least one absorption model; and
   determining whether the algae culture has a problem using at least one of: the peak absorption wavelength and the absorption ratio.

2. The method of claim 1, further comprising:
   illuminating the sample using at least one light source; and
   varying a temperature of the at least one light source to vary one or more wavelengths of light generated by the at least one light source.

3. The method of claim 1, wherein the identifying comprises:
   identifying a specified wavelength at which a smallest amount of light passes through the sample, the specified wavelength comprising the peak absorption wavelength.

4. The method of claim 1, wherein:
   the peak absorption wavelength comprises a peak absorption wavelength of chlorophyll a in the sample; and
   the absorption ratio comprises a ratio of chlorophyll a absorption and chlorophyll b absorption in the sample.

5. The method of claim 1, further comprising:
   repeating the measuring and identifying steps for multiple samples of the algae culture.

6. The method of claim 5, wherein determining whether the algae culture has the problem comprises:
   determining whether the peak absorption wavelength or the absorption ratio changes by a threshold amount within a specified time period.

7. The method of claim 1, further comprising:
   illuminating the sample using light within a specified range of wavelengths.

8. The method of claim 7, wherein the specified range of wavelengths is about 100 nm wide centered around 675 nm.

9. An apparatus comprising:
   at least one interface configured to receive measured intensities of light passing through a sample of an algae culture at different wavelengths; and
   at least one processing device configured to:
   identify, using the measured intensities, an average absorption wavelength of first and second types of chlorophyll in the sample and a peak absorption wavelength of the first type of chlorophyll;

identify an absorption ratio involving the first and second types of chlorophyll using the average absorption wavelength, the peak absorption wavelength, and at least one absorption model; and determine whether the algae culture has a problem using at least one of: the peak absorption wavelength and the absorption ratio.

10. The apparatus of claim 9, wherein the at least one processing device is further configured to control at least one temperature control device in order to adjust a temperature of at least one light source.

11. The apparatus of claim 9, wherein the at least one processing device is configured to identify a specified wavelength at which a smallest amount of light passes through the sample, the specified wavelength comprising the peak absorption wavelength.

12. The apparatus of claim 9, wherein the at least one processing device is further configured to identify the peak absorption wavelength and the absorption ratio for multiple samples of the algae culture.

13. The apparatus of claim 12, wherein the at least one processing device is configured to determine whether the algae culture has the problem by determining whether the peak absorption wavelength or the absorption ratio changes by a threshold amount within a specified time period.

14. The apparatus of claim 9, wherein the at least one processing device is further configured to control at least one light source to illuminate the sample using light within a specified range of wavelengths, the specified range of wavelengths about 100 nm wide centered around 675 nm.

15. The apparatus of claim 9, wherein:

the peak absorption wavelength comprises a peak absorption wavelength of chlorophyll a in the sample; and the absorption ratio comprises a ratio of chlorophyll a absorption and chlorophyll b absorption in the sample.

16. A non-transitory computer readable medium embodying a computer program, the computer program comprising computer readable program code for:

receiving measured intensities of light passing through a sample of an algae culture at different wavelengths;

identifying, using the measured intensities, an average absorption wavelength of first and second types of chlorophyll in the sample and a peak absorption wavelength of the first type of chlorophyll;

identifying an absorption ratio involving the first and second types of chlorophyll using the average absorption wavelength, the peak absorption wavelength, and at least one absorption model: and determining whether the algae culture has a problem using at least one of: the peak absorption wavelength and the absorption ratio.

17. The computer readable medium of claim 16, wherein the computer readable program code for identifying comprises:

computer readable program code for identifying a specified wavelength at which a smallest amount of light passes through the sample, the specified wavelength comprising the peak absorption wavelength.

18. The computer readable medium of claim 16, wherein the computer program further comprises computer readable program code for collecting the peak absorption wavelength and the absorption ratio for multiple samples of the algae culture.

19. The computer readable medium of claim 18, wherein the computer readable program code for determining whether the algae culture has the problem comprises computer readable program code for determining whether the peak absorption wavelength or the absorption ratio changes by a threshold amount within a specified time period.

20. The computer readable medium of claim 16, wherein:

the peak absorption wavelength comprises a peak absorption wavelength of chlorophyll a in the sample; and the absorption ratio comprises a ratio of chlorophyll a absorption and chlorophyll b absorption in the sample.

* * * * *